(12) United States Patent
Martelli et al.

(10) Patent No.: US 11,692,007 B2
(45) Date of Patent: Jul. 4, 2023

(54) AMINO DEPROTECTION USING 3-(DIETHYLAMINO)PROPYLAMINE

(71) Applicants: Alma Mater Studiorum—Università di Bologna, Bologna (IT); FRESENIUS KABI IPSUM S.R.L., Milan (IT)

(72) Inventors: Giulia Martelli, Bologna (IT); Paolo Cantelmi, Bologna (IT); Alessandra Tolomelli, Bologna (IT); Chiara Palladino, Bologna (IT); Lucia Ferrazzano, Bologna (IT); Walter Cabri, Milan (IT); Marco Macis, Milan (IT); Angelo Viola, Milan (IT); Antonio Ricci, Milan (IT)

(73) Assignees: Alma Mater Studiorum—Università di Bologna, Bologna (IT); Fresenius Kabi IPSUM S.r.l., Cassina de' Pecchi Milano (IT)

( * ) Notice: Subject to any disclaimer, the term of this patent is extended or adjusted under 35 U.S.C. 154(b) by 0 days.

(21) Appl. No.: 17/547,076

(22) Filed: Dec. 9, 2021

(65) Prior Publication Data

US 2022/0185842 A1  Jun. 16, 2022

(51) Int. Cl.
*C07K 1/06* (2006.01)
*C07K 7/06* (2006.01)
*A61K 38/00* (2006.01)

(52) U.S. Cl.
CPC ............ *C07K 1/063* (2013.01); *C07K 7/06* (2013.01); *A61K 38/00* (2013.01)

(58) Field of Classification Search
None
See application file for complete search history.

(56) References Cited

FOREIGN PATENT DOCUMENTS

WO  WO 2017/103275 A1  6/2017

OTHER PUBLICATIONS

Pribylka et al. ('Environmentally friendly SPPS II: scope of green Fmoc removal protocol using NaOH and its application for synthesis of commercial drug triptorelin' JOC Jun. 2020 v85 pp. 8798-8811) (Year: 2020).*
Carping et al., "Tris(2-aminoethyl)amine as a Substitute for 4-(Aminomethyl)piperidine in the FMOC-Polyamine Approach to Rapid Peptide Synthesis," Journal of Organic Chemistry, American Chemical Society, Washington, DC, vol. 55, No. 5, pp. 1673-1675 (1990).
Greene et al., "9-Fluorenylmethyl Carbamate (Fmoc-NR$_2$) (Chart8), t-Butyl (BOC) Carbamate: (CH$_3$)$_3$COC(O)NR$_2$ (Chart 8)," Protective Groups In Organic Synthesis, John Wiley & Sons, Inc, New York, NY, pp. 506-507, 518-523 (1999).
Martelli et al., "Replacing piperidine in solid phase peptide synthesis: effective Fmoc removal by alternative bases," *Green Chemistry* 23: 8096-8107 (2021).
European Patent Office, Extended European Search Report in European Patent Application No. 20 21 3533 (Jun. 7, 2021.

\* cited by examiner

*Primary Examiner* — Ronald T Niebauer
(74) *Attorney, Agent, or Firm* — Leydig, Voit & Mayer, Ltd.

(57) ABSTRACT

The invention provides a method for the cleavage of Fmoc group characterized by using a solution comprising 3-(diethylamino)propylamine. In particular, it provides a method for the preparation of peptides in solid phase wherein Fmoc protected amino acids are used and the Fmoc group is cleaved by a solution comprising 3-(diethylamino)propylamine.

14 Claims, 5 Drawing Sheets

Specification includes a Sequence Listing.

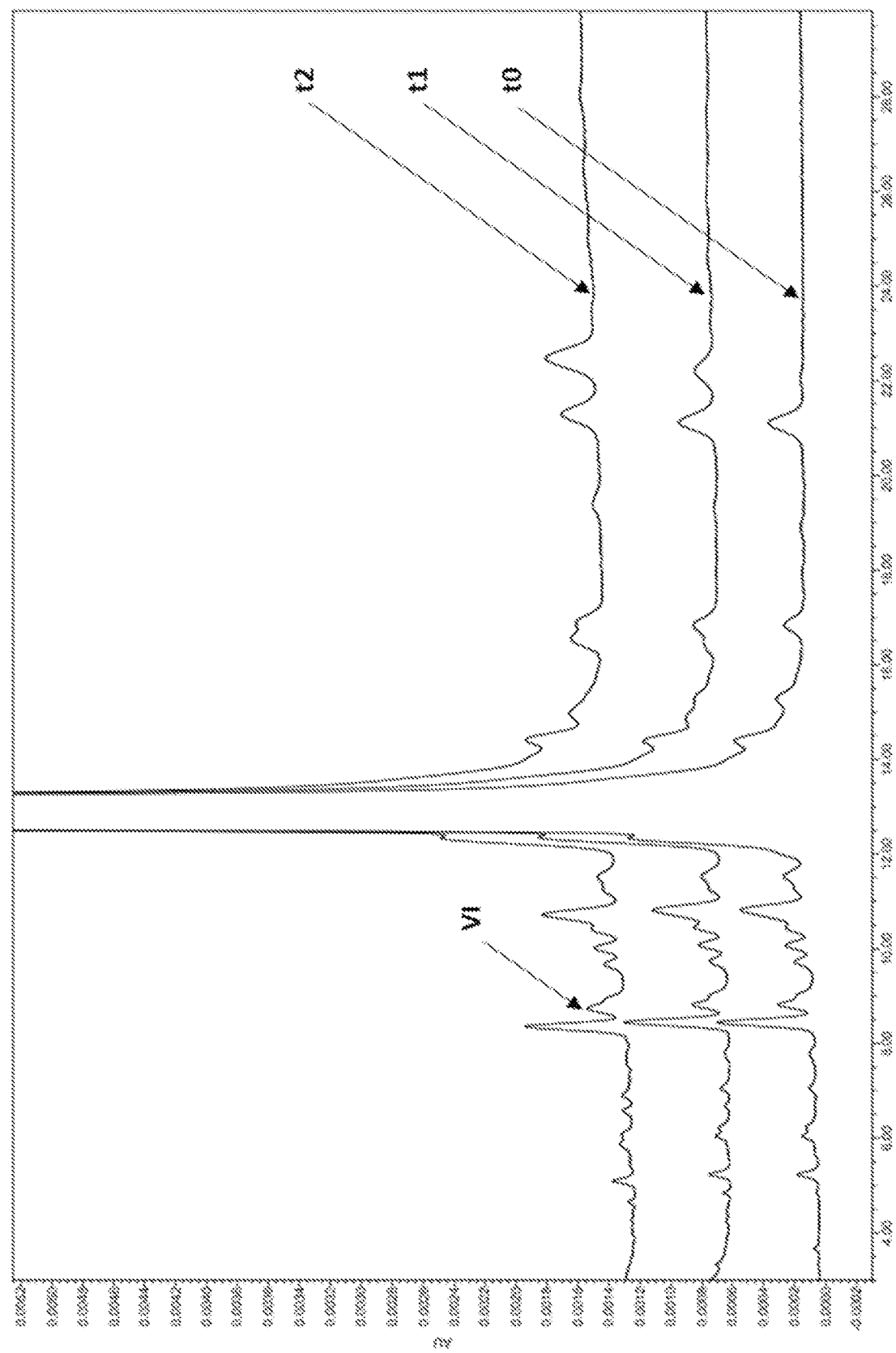

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Linear Octreotide
<220> FEATURE:
<221> NAME/KEY: MOD_RES
<222> LOCATION: (1)..(1)
<223> OTHER INFORMATION: Xaa is D-Phe
<220> FEATURE:
<221> NAME/KEY: MOD_RES
<222> LOCATION: (4)..(4)
<223> OTHER INFORMATION: Xaa is D-Trp
<220> FEATURE:
<221> NAME/KEY: MOD_RES
<222> LOCATION: (8)..(8)
<223> OTHER INFORMATION: C-terminal Threoninol

<400> SEQUENCE: 1

Xaa Cys Phe Xaa Lys Thr Cys Thr
1               5

<210> SEQ ID NO 2
<211> LENGTH: 6
<212> TYPE: PRT
<213> ORGANISM: Artificial Sequence
<220> FEATURE:
<223> OTHER INFORMATION: Model hexapeptide

<400> SEQUENCE: 2

Ala Lys Asp Gly Tyr Ile
1               5
```

AMINO DEPROTECTION USING 3-(DIETHYLAMINO)PROPYLAMINE

CROSS-REFERENCE TO RELATED APPLICATION

This application claims the benefit of European Patent Application No. 20213533.1, filed Dec. 11, 2020, the disclosure of which is incorporated herein by reference in its entirety for all purposes.

INCORPORATION BY REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,096 byte ASCII (Text) file named "758192_SequenceListing", created on Dec. 8, 2021.

BACKGROUND OF THE INVENTION

The invention relates to the field of amino function protection chemistry. In particular, it relates to a method for the cleavage of the Fmoc amino protective group. More in particular, it relates to a method for cleaving the Fmoc amino protective group in the synthesis of peptides e.g. in solid phase peptide synthesis (SPPS).

The Fmoc group is one of the most commonly used amino protective groups. The most frequently used method for removing the Fmoc group is the treatment of the protected chemical compound with a piperidine solution in 1,1-dimethylformamide (DMF). The Fmoc group is one of the most commonly used alpha-amino protective groups in the synthesis of peptides. It is particularly common to use the Fmoc group as alpha-amino protective group in the elongation of sequences in SPPS. The standard procedure for removing the Fmoc group after each amide bond formation cycle of the stepwise peptide synthesis is the treatment of the growing peptide with a solution of 20% piperidine in DMF.

However, piperidine is a controlled substance as it is employed as a precursor in the illicit synthesis of narcotic drugs and psychotropic substances, like fentanyl and phencyclidine (PCP, also referred to as "angel dust"), under international control. For this reason, it is included in the Red List of the International Narcotics Control Board (INCB, see 17$^{th}$ Ed, January 2020).

In addition, piperidine, which needs to be used in high excess for cleavage of Fmoc, is a highly toxic compound. The acute oral toxicity is high in many species of test animals. The $LD_{50}$ values in mice, rabbits and rats are 30, 145 and 400 mg/kg, respectively.

There is therefore a need for new synthesis routes addressing the drawbacks of using piperidine, which are amenable to the application in the manufacturing of chemicals, in particular of peptides, at an industrial scale and without any restrictions to its use.

BRIEF SUMMARY OF THE INVENTION

The problem is solved by the present invention, providing a method for cleaving Fmoc from one or more Fmoc protected amino groups, wherein the method comprises a step of contacting the Fmoc protected amino groups with a solution comprising 3-(diethylamino)propylamine, also known as DEAPA.

The present invention further provides a method for the cleavage of the Fmoc amino protective group by using a solution comprising DEAPA in the synthesis of peptides, in particular in solid phase peptide synthesis.

Further, the present invention provides a method for the preparation of a peptide by Fmoc-based solid phase peptide synthesis, wherein the method comprises a step of contacting the Fmoc protected amino groups with a solution comprising 3-(diethylamino)propylamine, thereby cleaving the Fmoc from one or more Fmoc protected amino groups.

Surprisingly, such methods provide peptides with an overall improved purity.

In one embodiment, the present invention provides a method for the preparation of peptides using solid phase peptide synthesis, wherein the peptide comprises at least one aspartic acid amino acid, the method being characterized by using a solution comprising DEAPA for the cleavage of the Fmoc amino protective group. More particularly, the method is characterized by comprising a step of contacting the Fmoc protected amino group with a solution comprising DEAPA.

In a further embodiment, the present invention provides a method for the preparation of degarelix in solid phase peptide synthesis, which is characterized by using a solution comprising DEAPA for the cleavage of one or more Fmoc amino protective groups.

In preferred embodiments, the methods according to the invention are characterized by using a 10% DEAPA solution for the cleavage of the Fmoc amino protective group. Even more preferably the solution is 10% DEAPA in DMF.

In particular, the present invention provides a method for the preparation of a peptide in solid phase peptide synthesis, characterized by using a 10% DEAPA solution in DMF for cleaving Fmoc amino protective groups.

BRIEF DESCRIPTION OF THE DRAWINGS

FIG. 5: Superimposed HPLC profiles of degarelix in the presence of DEAPA at t0, 8 hr (t1), and 24 hr (t2) (Example 8).

DETAILED DESCRIPTION OF THE INVENTION

Figure 1:
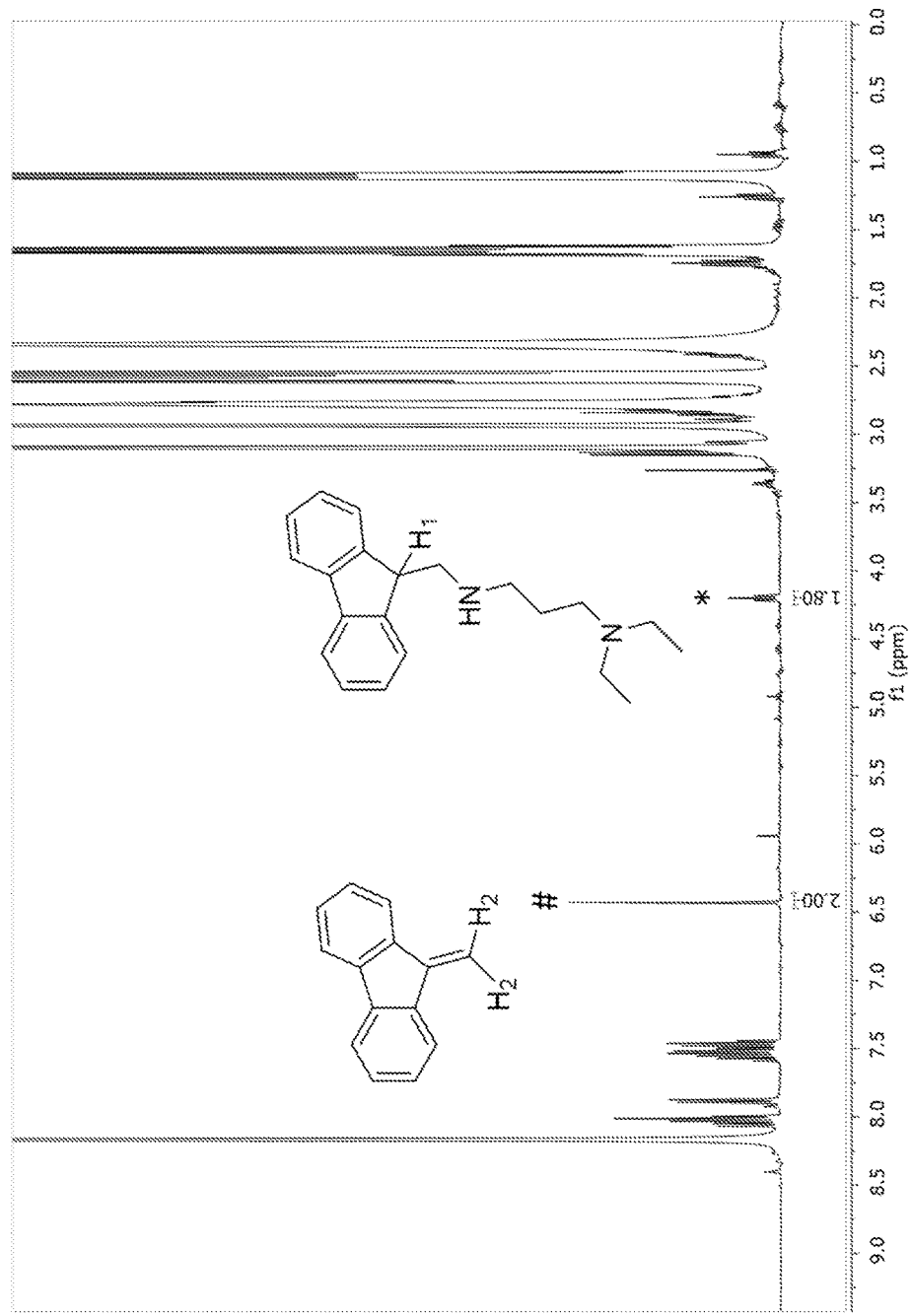
FIG. 1: $^1$H NMR after 20% DEAPA deprotection of Fmoc-Gly-Trt-PS resin in DMF-d6 (Example 1): the peak indicated with * corresponds to $H_1$ signal of DBF-DEAPA adduct; the peak indicated with # corresponds to $H_2$ signals of DBF; signals at 7.5-8.0 ppm are referred to a mixture of DBF and DBF-DEAPA aromatic protons. Calculated ratio of DBF/DBF-DEAPA adduct is 1/1.8.
Figure 2:
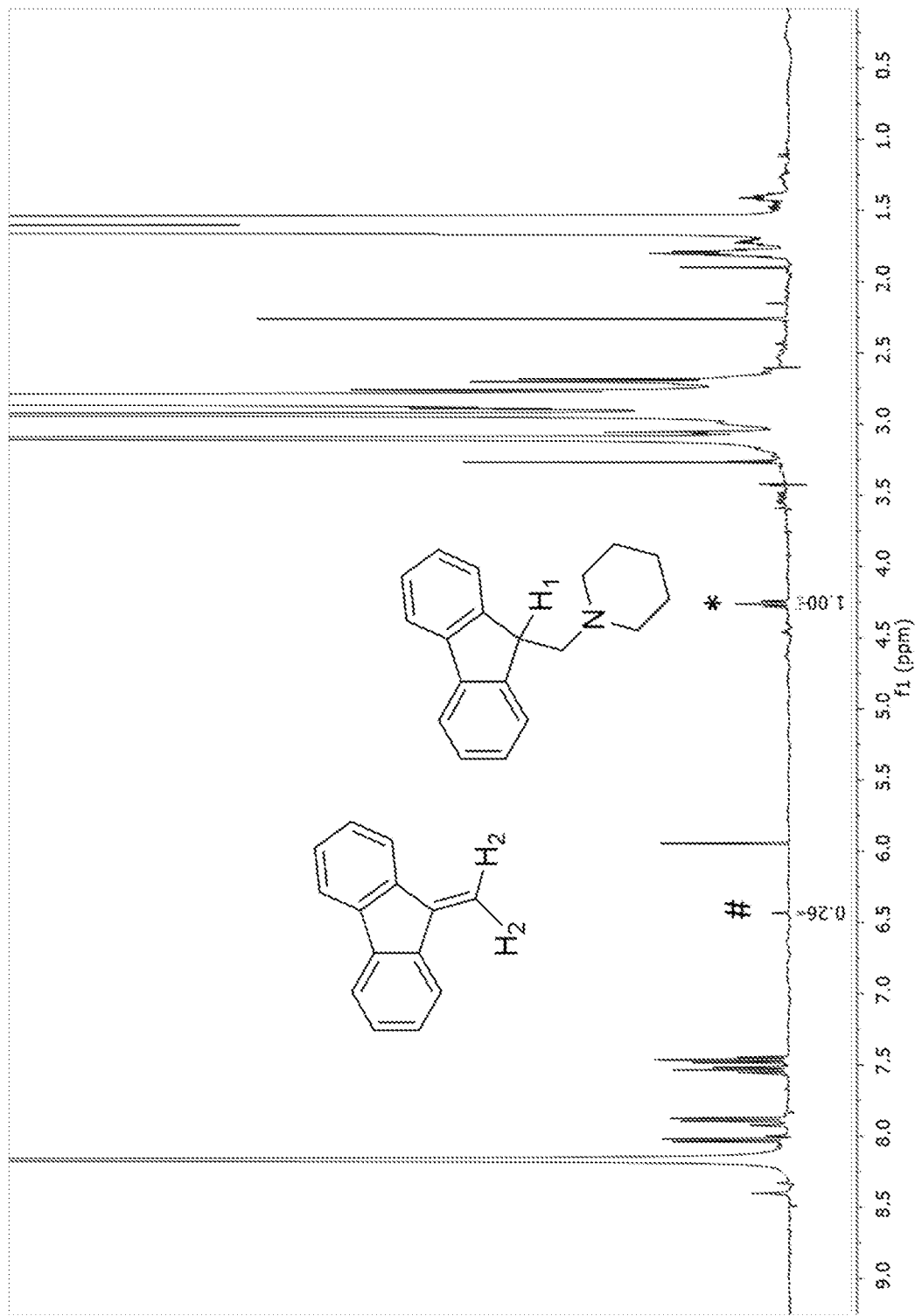
FIG. 2: $^1$H NMR after 20% piperidine deprotection of Fmoc-Gly-Trt-PS resin in DMF-d6 (Example 1): the peak indicated with * corresponds to $H_1$ signal of DBF-piperidine adduct; the peak indicated with # corresponds to $H_2$ signals of DBF; signals at 7.5-8.0 ppm are referred to a mixture of DBF and DBF-piperidine aromatic protons. Calculated ratio of DBF/DBF-piperidine adduct is 1/7.7.

Fmoc, i.e. 9-fluorenylmethyloxycarbonyl, herein also referred to as Fmoc group, is employed as a protecting group for amino functions. For decades the standard agent for Fmoc cleavage is piperidine, and even though its toxicity and its status as a scheduled substance (controlled substance) have always been regarded to be disadvantageous, none of the bases which have been proposed for Fmoc cleavage so far became a new standard.

The terms "amino function" and "amino group" refer to any primary or secondary amines, including aliphatic—acyclic and cyclic—and aromatic amines, which can be protected by the Fmoc group. Preferably, such an amino function is a primary aliphatic amine, more preferably the alpha-amino group of an amino acid or of a peptide.

In particular, the Fmoc group is employed as protection for the alpha-amino group of the amino acids used as building blocks in the synthesis of peptides, both in liquid phase peptide synthesis (LPPS) and in SPPS. The chemical conditions required for its cleavage are generally orthogonal to the conditions required for the cleavage of the amino acids side-chain protecting groups. The latter are commonly removed after all the elongation steps of the peptide chain are concluded. This generally occurs with simultaneous cleavage of the peptide chain from the solid support when the peptide is synthesized in SPPS.

Such peptide preparation in solid phase can be carried out either as a stepwise, or a fully Fmoc-based SPPS, wherein the amino acids are coupled one by one to the growing peptide sequence attached to a solid support, or as a Fmoc-based Convergent SPPS (CSPPS), wherein at least two peptide fragments, independently prepared, are coupled together to form amide bonds and longer peptide fragments, until the final sequence is finally obtained, wherein one of the two fragments involved in a coupling reaction is attached to a solid support.

The terms "Fmoc-based SPPS" or "Fmoc-based peptide synthesis" refer to a peptide synthesis wherein amino acids are employed, where the alpha-amino group is protected by the Fmoc group.

The Fmoc group is also used as protection for amino functions in side-chains in a Boc-based SPPS, i.e. when amino acids are employed, whose alpha-amino group is protected by the Boc group. In this case, as the cleavage of Boc requires acidic conditions, the protection of side-chains with Fmoc provides the required orthogonality for the deprotection of alpha-amino groups without removing the side-chain protections. Also in this scenario DEAPA can be used to deprotect the side-chain amino function.

The terms "peptide fragment" and "fragment", as used herein, describe a partial sequence of amino acids, with a minimum length of 2 amino acids, relative to the sequence of the target peptide. A peptide fragment is generally protected at the side-chain as well as at the N-terminal alpha-amino group not involved in a coupling reaction. The N-terminal alpha-amino group is preferably protected by Fmoc group.

The terms "amine deprotecting agent" and "Fmoc cleaving agent" are herein used as synonyms and refer to the reagents used in the present disclosure for the cleavage of Fmoc amino protective groups.

The terms "cleavage" and "removal", as well as the verbs "cleave" and "remove" are herein used as synonyms and refer to the breaking of the chemical bonds occurring during deprotection of Fmoc-protected amino groups.

The present invention thus provides a method for the preparation of a peptide, or a pharmaceutically acceptable salt thereof, by using solid phase peptide synthesis characterized by using a solution comprising DEAPA for cleaving Fmoc amino protective groups from Fmoc-protected alpha-amino groups.

The invention also provides a peptide prepared by any aspect of the method of the present invention. Thus, the invention provides a peptide or a pharmaceutically acceptable salt thereof prepared by a method comprising synthesizing a peptide comprising at least one Fmoc-protected amino acid, and cleaving the Fmoc group from the amino acid with a solution comprising DEAPA. In certain embodiments, the peptide is synthesized by solid phase peptide synthesis. In some embodiments, the peptide is selected from the group consisting of degarelix, octreotide, exenatide, etelcalcetide and glucagon.

The invention also provides a pharmaceutical composition comprising a peptide prepared by any aspect of the method of the present invention and a pharmaceutically acceptable carrier. In some embodiments, the peptide is selected from the group consisting of degarelix, octreotide, exenatide, etelcalcetide and glucagon.

The invention also provides a peptide, or pharmaceutically acceptable salt thereof, comprising not more than 1000 ppm DEAPA, e.g., not more than 750 ppm DEAPA, not more than 500 ppm DEAPA, not more than 250 ppm DEAPA, not more than 150 ppm DEAPA, or not more than 100 ppm DEAPA. In other embodiments, the invention provides a peptide, or pharmaceutically acceptable salt thereof, comprising more than 1 ppm DEAPA, e.g., more than 10 ppm DEAPA, more than 50 ppm DEAPA, e.g., more than 125 ppm DEAPA, more than 200 ppm DEAPA, more than 400 ppm DEAPA, or more than 800 ppm DEAPA. In yet other embodiments, the invention provides a peptide, or pharmaceutically acceptable salt thereof, comprising DEAPA in an amount bounded by one of the foregoing values, e.g., 1 ppm to 1000 ppm DEAPA, 10 ppm to 500 ppm DEAPA, 50 ppm to 250 ppm DEAPA, 125 ppm to 750 ppm DEAPA, 125 ppm to 500 ppm DEAPA, or 200 ppm to 500 ppm DEAPA. In some embodiments, the peptide is selected from the group consisting of degarelix, octreotide, exenatide, etelcalcetide and glucagon.

DEAPA has surprisingly proven to be suitable for the cleavage of Fmoc amino protective groups. It has been shown to be superior to the use of piperidine in peptide synthesis, wherein it can be used both in liquid and in solid phase, in particular in SPPS. It is a less toxic and more environmentally friendly chemical and proved to perform as a fast, safe and efficient reagent.

3-(diethylamino)propylamine (I) chemical structure is depicted below:

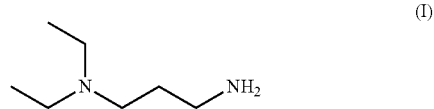

(I)

Comparison DEAPA/Other Bases Fmoc Cleavage

The reaction rates of DEAPA and piperidine in the deprotection reaction removing Fmoc from a model amino acid like Fmoc-Phe-OH were compared in two different solvents, DMF and NBP (i.e. N-butyl-1-pyrrolidone), and at two different concentrations, 10% and 20%. Other amines were also tested, namely 1,1,3,3-tetramethylguanidine (TMG) and tert-butylamine (TBA). The results proved that DEAPA is as suitable for Fmoc cleavage as the other amines tested.

The mechanism of Fmoc cleavage is depicted in the following:

Scheme 1

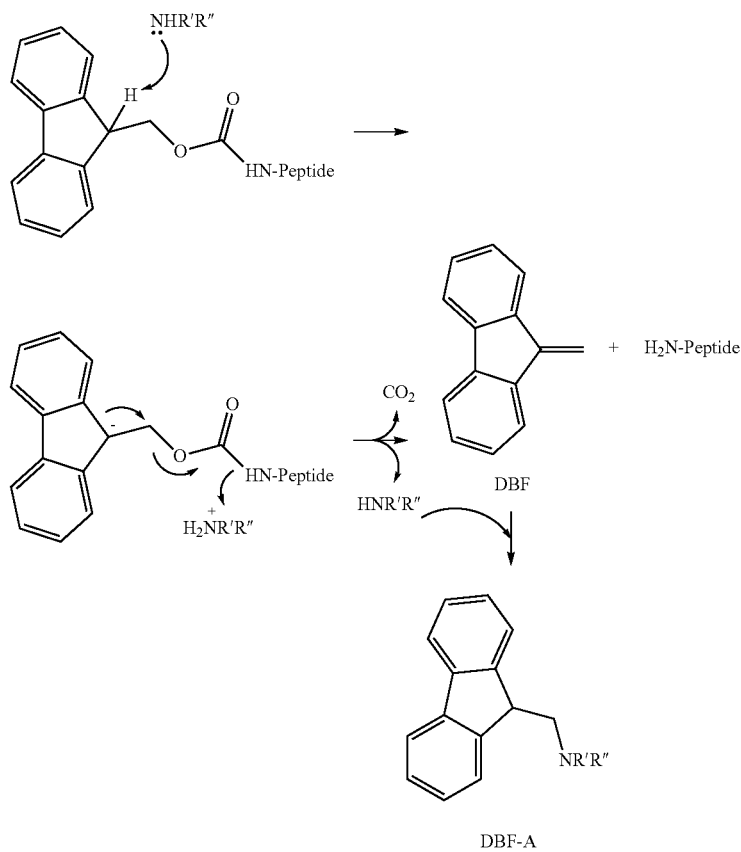

Dibenzofulvene (DBF), which is formed in the first step, is a reactive species and can further react with the amine deprotecting agent to form a DBF-amine adduct (DBF-A). This prevents the possible side-reaction wherein DBF reacts with the free alpha-amino group of the peptide under preparation or with any other reactive species which might be present in the reaction mixture. It was surprisingly observed that piperidine and DEAPA were able to form the DBF-amine adduct, whereas TMG and TBA did not form the DBF adduct. DEAPA is therefore capable to act as a scavenging agent towards DBF and therefore prohibits side reactions caused by DBF. In this regard, DEAPA surprisingly reacts in the same way as piperidine, the standard cleaving agent for Fmoc.

DEAPA was further tested for any impact in racemization in Fmoc-based SPPS. Cysteine is known in the art to be extraordinarily prone to undergo racemization during peptide synthesis. At first, H-Phe-L-Cys-Gly-OH and H-Phe-D-Cys-Gly-OH were prepared as standards, as described in Example 2. Then, full Fmoc-based SPPS of H-Phe-L-Cys-Gly-OH was performed in parallel by using DEAPA or piperidine to remove the Fmoc groups (30% base solution), as described in Example 3. No substantial difference in the racemization ratio was observed between DEAPA and piperidine, as in both experiments the D/L ratio % (or racemization ratio %) was below 0.1.

In the following, the full Fmoc-based SPPS preparation of representative peptides by using DEAPA as a Fmoc cleaving agent is described.

For example, linear octreotide (II), i.e. H-D-Phe-Cys-Phe-D-Trp-Lys-Thr-Cys-Thr-ol (SEQ ID NO: 1), was prepared in three different parallel experiments, by using 10% DEAPA in DMF, 20% piperidine in DMF or 20% piperidine in NBP for the cleavage of Fmoc groups. The final product obtained by using DEAPA showed an increased purity, as described in detail in Example 4.

II

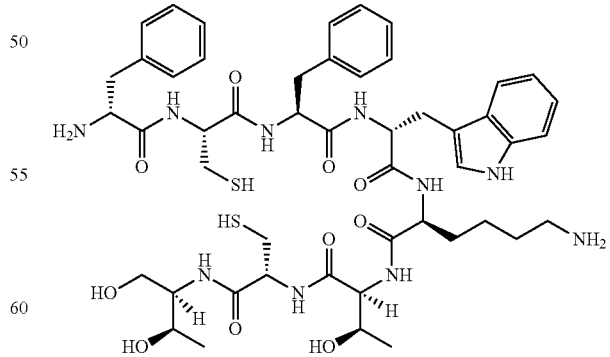

The invention also provides octreotide, or a pharmaceutically acceptable salt thereof, prepared by a method comprising synthesizing a peptide comprising at least one Fmoc-protected amino acid, and cleaving the Fmoc group from the amino acid with a solution comprising DEAPA. In certain embodiments, the peptide is synthesized by solid phase peptide synthesis.

The invention further provides octreotide, or pharmaceutically acceptable salt thereof, comprising not more than 1.2% total impurities, e.g., not more than 1.0%, not more than 0.8%, not more than 0.7%, not more than 0.6%, or not more than 0.5% of total impurities relative to the octreotide or a pharmaceutically acceptable salt thereof.

By analogue SPPS procedure, other peptides, like for instance glucagon, exenatide, etelcalcetide and the like, could be prepared by using the method according to the present invention.

One of the concerns in peptide synthesis is the formation of aspartimide side-products. Basic conditions, which are mandatory for Fmoc group cleavage, may also favor the formation of unwanted aspartimide derivatives during Fmoc-based SPPS and their occurrence generally increases with the number of Fmoc cleavage cycles after the introduction of an aspartic acid residue (Asp) in the peptide chain. The aspartimide ring in the side product may then be opened by nucleophilic attack with formation of further unwanted chemical species, as shown in the following scheme:

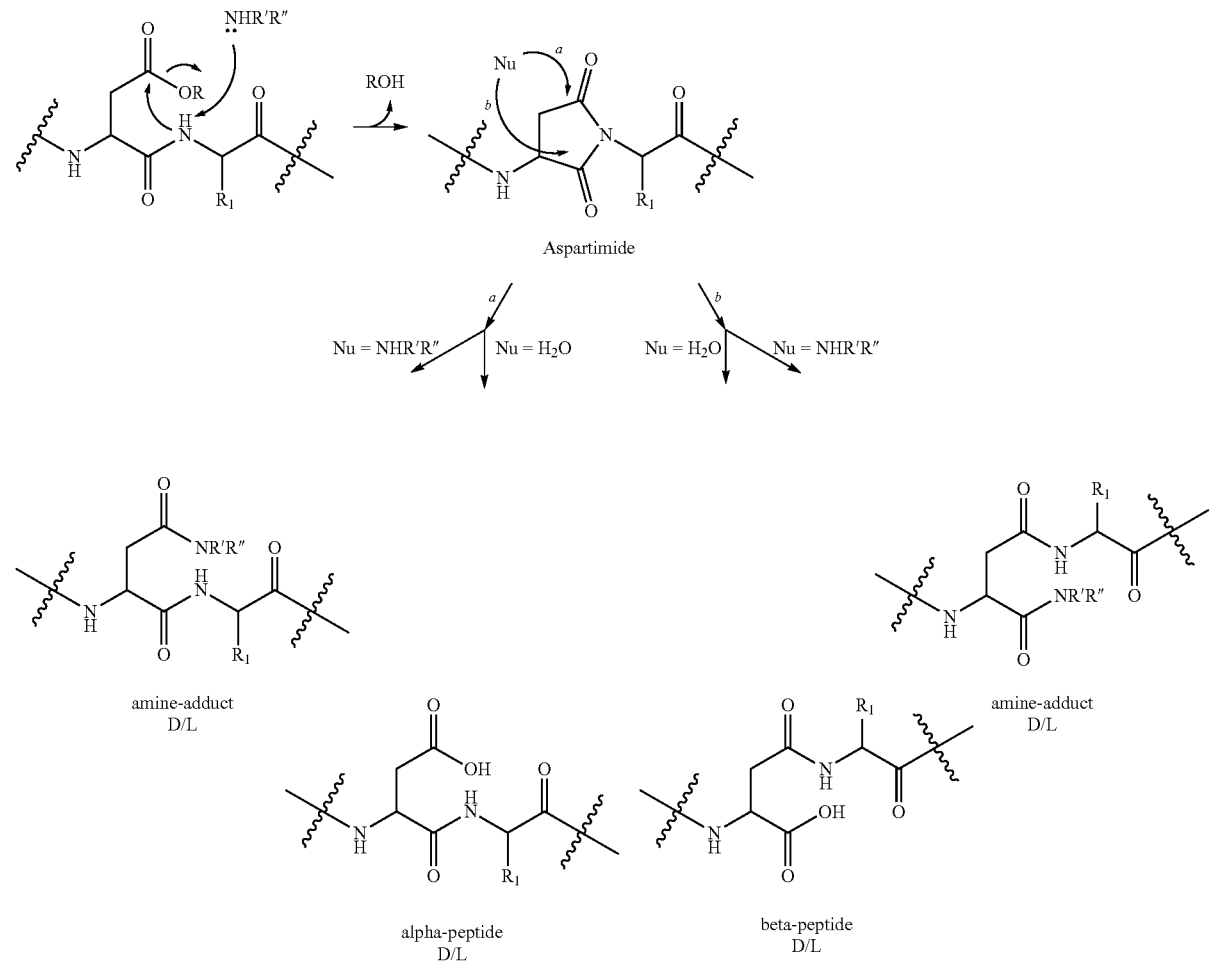

The alpha-peptide may correspond to the target peptide, although racemization at Asp might occur.

To analyze the suitability of DEAPA in such a scenario, a model peptide was prepared and then contacted under the basic conditions either with piperidine, or another suitable amine, or with DEAPA for extended periods of time.

The model hexapeptide H-Ala-Lys-Asp-Gly-Tyr-Ile-OH (III, SEQ ID NO: 2, Scheme 3) was prepared by full Fmoc-based SPPS by using 20% piperidine in DMF, and aspartimide impurity (IV, Scheme 3) content was determined in the final compound, which was found to be 2.6% (HPLC, Example 5).

Scheme 3

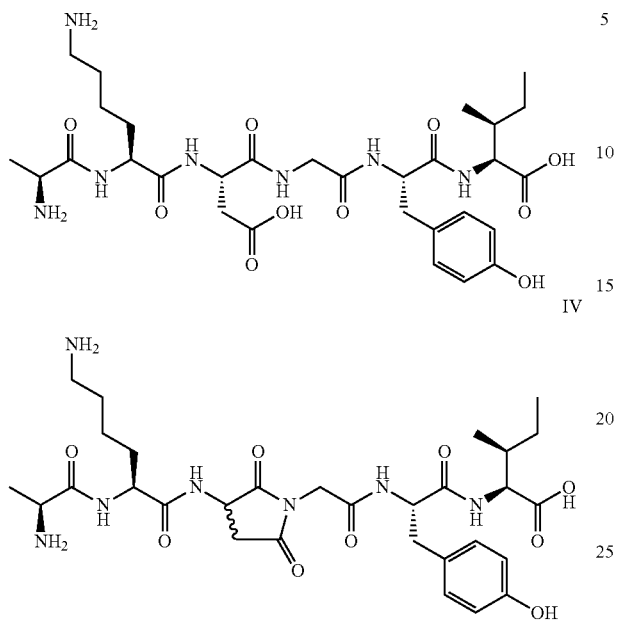

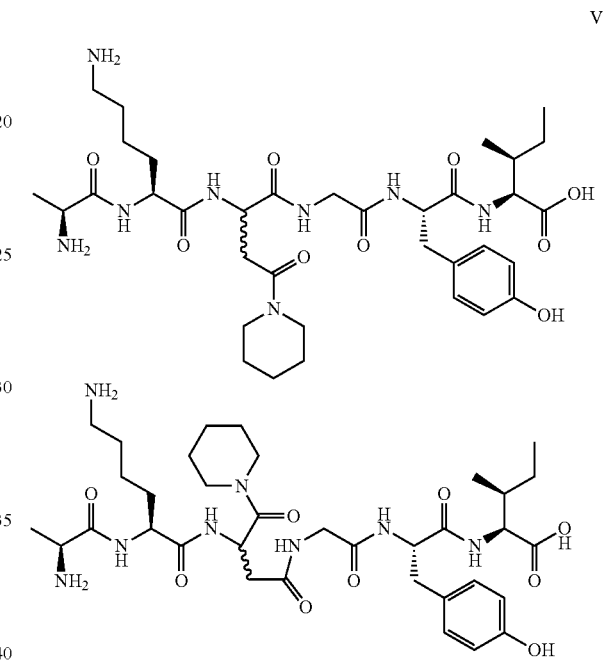

A stress test was then performed whereby the model peptide was submitted to basic conditions to simulate repeated alpha-amino deprotection cycles. Resin-bound H-Ala-Lys-Asp-Gly-Tyr-Ile-OH (still bearing side-chain protections) was treated in parallel with 20% piperidine, 10% DEAPA, 5% TMG or 20% TBA solutions, in DMF or NBP, for 4 h at RT.

As shown in Scheme 2 above, the formation of the aspartimide side-product may be followed by nucleophilic attack onto the aspartimide ring with formation of further by-products, like amine-adducts (amine-mediated ring-opening) and alpha- and beta-peptides (water-mediated ring-opening).

The hexapeptide samples obtained after such treatments with the Fmoc cleavage solutions were analyzed by HPLC and the results are shown in Table 1 (for detailed experimental procedure, see Example 6).

TABLE 1

HPLC purity (A %) of H-Ala-Lys-Asp-Gly-Tyr-Ile-OH (III, SEQ ID NO: 2)

| Entry | Base | Solvent | III (A %) | Aspartimide (IV) (A %) | Piperidides (V) (A %) | Δ Asp (A %) |
|---|---|---|---|---|---|---|
| | Starting point (after synthesis in DMF with 20% pip) | | 97.4 | 2.6 | — | |
| 1 | 20% piperidine | DMF | 86.5 | 7.2 | 6.3 | 10.9 |
| 2 | 10% DEAPA | DMF | 89.9 | 10.1 | — | 7.5 |
| 3 | 5% TMG | DMF | 14.5[a] | 85.5 | — | 82.9 |
| 4 | 20% TBA | DMF | 70.7 | 29.3 | — | 26.7 |
| 5 | 20% piperidine | NBP | 90.0 | 7.1 | 2.9 | 7.4 |
| 6 | 10% DEAPA | NBP | 95.8 | 4.2 | — | 1.6 |

TABLE 1-continued

HPLC purity (A %) of H-Ala-Lys-Asp-Gly-Tyr-Ile-OH (III, SEQ ID NO: 2)

| Entry | Base | Solvent | III (A %) | Aspartimide (IV) (A %) | Piperidides (V) (A %) | Δ Asp (A %) |
|---|---|---|---|---|---|---|
| 7 | 5% TMG | NBP | 27.1[a] | 72.9 | — | 70.3 |
| 8 | 20% TBA | NBP | 80.0 | 20.0 | — | 17.4 |

[a]sum of alpha- and beta-peptide

When piperidine was used, the formation of piperidides (V) was observed.

The use of DEAPA resulted in the formation of the corresponding by-products in traces only, and those are not listed in Table 1.

Cleavage with TMG resulted in the formation of the beta-peptide, co-eluting with the alpha-peptide, corresponding to the target peptide (III).

In Table 1, Δ Asp indicates the amount of additional overall aspartimide impurities (comprising piperidides by-products) resulting from the stress test relative to the initial aspartimide amount (2.6%). This value proved to be lower when DEAPA was used, compared to the other tested amines, in the respective solvent.

As a consequence, the purity of the target peptide (III) is higher in the samples treated with the DEAPA solution.

Accordingly, the present invention provides a method for the cleavage of Fmoc amino protective groups characterized by using a solution comprising 3-(diethylamino)propylamine.

The present invention also provides a method for the preparation of a peptide characterized by using a solution comprising 3-(diethylamino)propylamine for cleaving Fmoc amino protective groups.

Furthermore, the present invention provides a method for the preparation of a peptide by solid phase peptide synthesis characterized by using a solution comprising 3-(diethylamino)propylamine for cleaving Fmoc amino protective groups.

Preferably, the concentration of DEAPA ranges from 5 to 30%, more preferably from 10 to 20%, most preferably it is 10%. Preferably, the solvent is a polar aprotic solvent, more preferably it is selected from the group consisting of DMF, NBP, NMP (i.e. 1-methyl-2-pyrrolidone) or similar solvents, or mixtures thereof. In the most preferred embodiment, the solution is a 10% concentration of DEAPA in DMF.

Wherein throughout the present disclosure concentration values are given in % these refer to vol %.

In an especially preferred embodiment, the present invention provides a method for the cleavage of Fmoc amino protective groups characterized by using a 10% DEAPA solution in DMF.

The use of DEAPA also proved to be advantageous in the synthesis of Degarelix (VI). Degarelix is identified by the sequence:

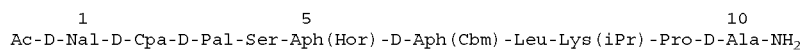
Ac-D-Nal-D-Cpa-D-Pal-Ser-Aph(Hor)-D-Aph(Cbm)-Leu-Lys(iPr)-Pro-D-Ala-NH₂ wherein the numbers indicate the amino acid (aa) positions, starting from N-terminal aa (D-Nal) to C-terminal aa (D-Ala).

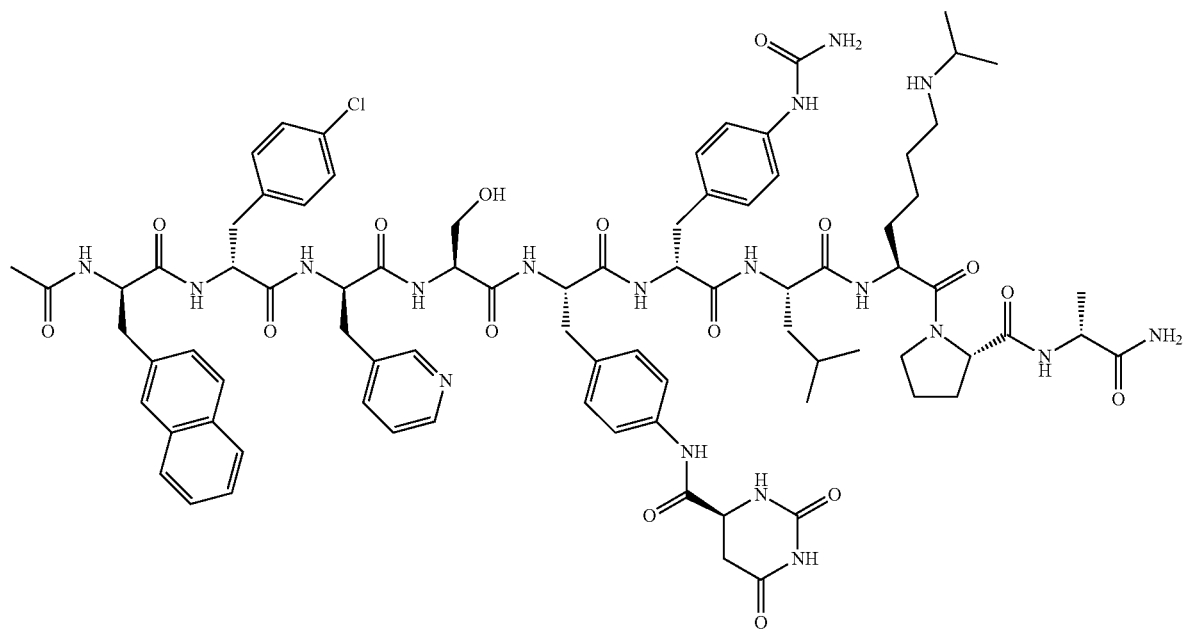

VI

One of the main problems in the preparation of degarelix is the high sensitivity of the (L)dihydroorotic acid (indicated as Hor) moiety of the Aph(Hor) residue in position 5 of the sequence in the presence of an aqueous basic solution. Under these conditions, a rapid rearrangement of the 6-membered Hor ring occurs, with formation of a 5-membered hydantoin ring.

The stability of degarelix (VI) to hydantoin rearrangement was tested in a DEAPA solution to monitor any formation of its hydantoin impurity (VII).

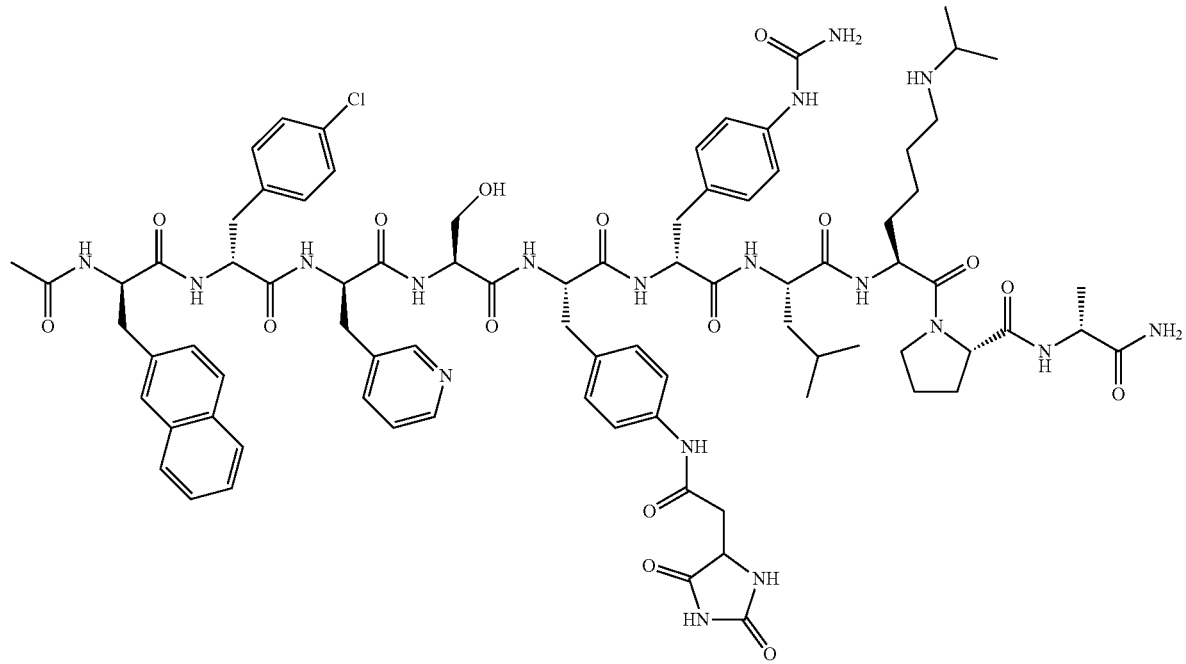

VII

Figure 3:
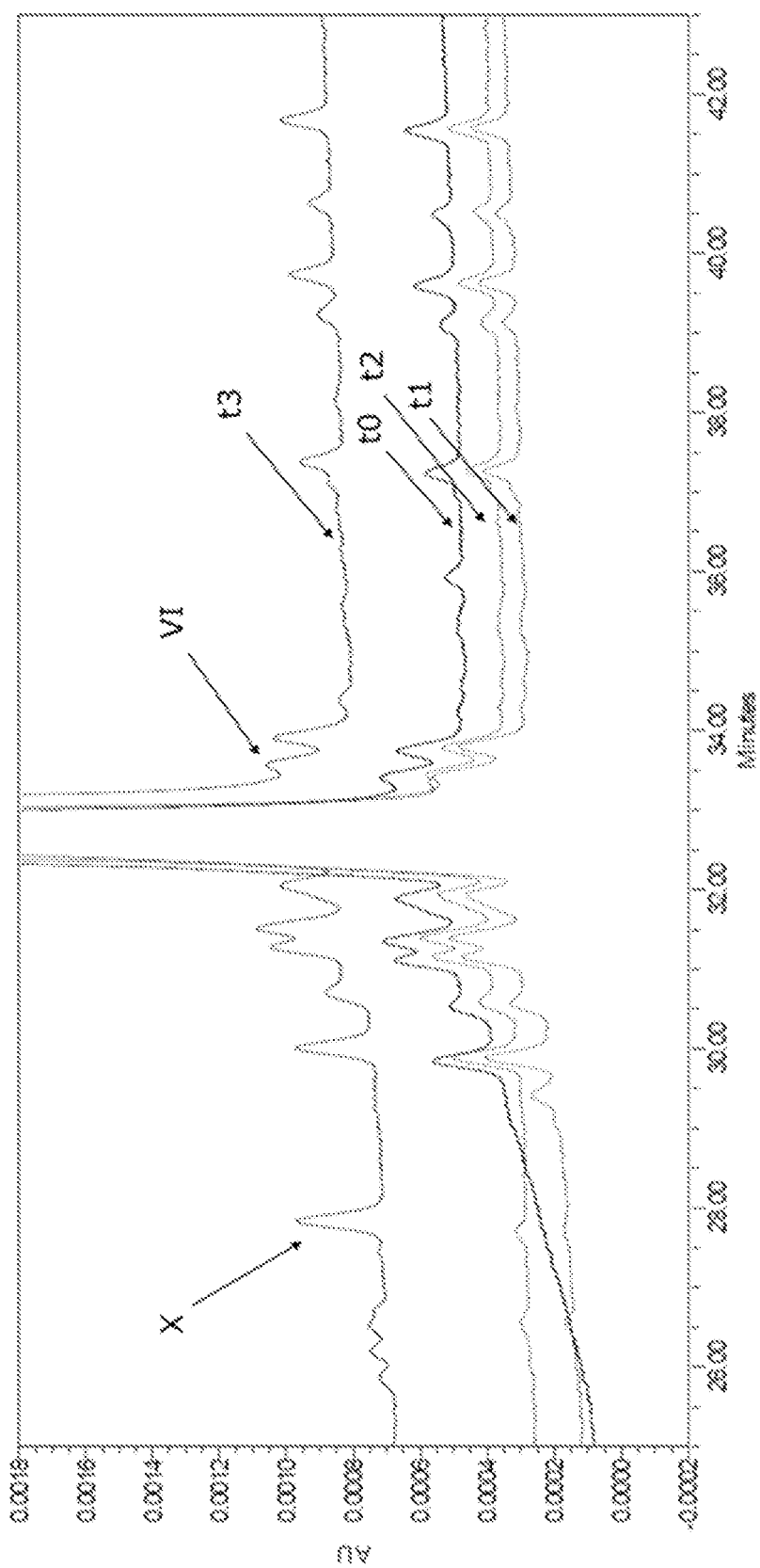
FIG. 3: Superimposed HPLC profiles of degarelix at t0, t1, t2 and t3 (Test 1, Example 7).
Figure 4:
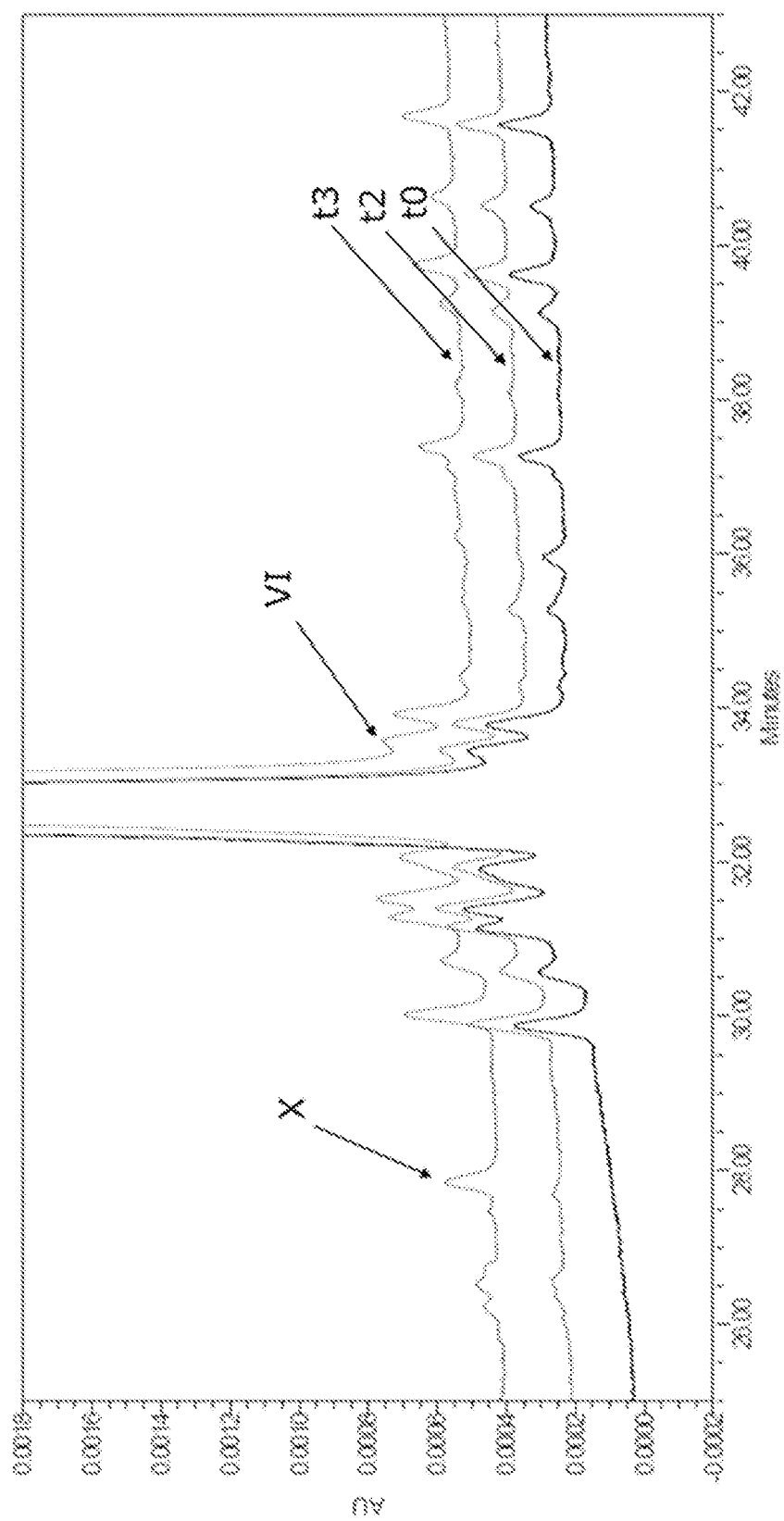
FIG. 4: Superimposed HPLC profiles of degarelix at t0, t2 and t3 (Test 2, Example 7)

Degarelix was kept in a solution of 10% DEAPA in DMF for 24 h to simulate conditions corresponding to those used for removal of Fmoc group during full SPPS. Samples were analyzed by HPLC at four checkpoints up to 24 h and the four HPLC profiles obtained were compared as shown in FIG. 3 and FIG. 4 (for detailed experimental procedure, see Example 7).

No significant degradation of degarelix was observed. In particular, no increase of hydantoin impurity (VI) was detected.

Accordingly, the present invention provides a method for the preparation of degarelix by solid phase peptide synthesis characterized by using a solution comprising DEAPA for cleaving Fmoc amino protective groups, wherein the solid phase synthesis is either a full SPPS or a CSPPS.

The invention also provides degarelix, or a pharmaceutically acceptable salt thereof, prepared by a method comprising synthesizing a peptide comprising at least one Fmoc-protected amino acid, and cleaving the Fmoc group from the amino acid with a solution comprising DEAPA. In certain embodiments, the peptide is synthesized by solid phase peptide synthesis.

Preferably, in the preparation of degarelix the concentration of DEAPA ranges from 5 to 30%, more preferably from 10 to 20%, most preferably it is 10%. Preferably, the solvent is a polar aprotic solvent, more preferably DMF, NBP, NMP (i.e. 1-methyl-2-pyrrolidone) or the like, or mixtures thereof.

In an especially preferred embodiment, the present invention provides a method for the synthesis of degarelix characterized by using a 10% DEAPA solution in DMF for the cleavage of Fmoc amino protective groups.

In a preferred embodiment, the synthesis of degarelix according to the present invention is performed by using at least one of the compounds selected from the group consisting of Fmoc-Aph(Hor)-OH, Fmoc-Aph(PG)-OH, Fmoc-Phe(NO$_2$)—OH, Fmoc-D-Phe(NO$_2$)—OH and a peptide fragment comprising one or more of Aph(Hor), Phe(NO$_2$) and D-Phe(NO$_2$). PG is an amino protective group selected from the group consisting of tert-butyloxycarbonyl, formyl, allyloxycarbonyl and benzyloxycarbonyl. In particular, the present invention provides a method for the preparation of degarelix by full Fmoc-based SPPS following the approach described in WO2017103275, example 2, page 34, characterized by using a solution comprising DEAPA for cleaving Fmoc amino protective groups instead of piperidine.

In another embodiment, the present invention provides the use of 3-(diethylamino)propylamine for cleaving the Fmoc amino protective group. In particular, it provides the use of 3-(diethylamino)propylamine for cleaving the Fmoc amino protective group in peptide synthesis, preferably in solid phase peptide synthesis.

Compared to piperidine which has been the standard cleaving agent for Fmoc for decades, DEAPA has a lower toxicity (LD$_{50}$ rat=830 mg/kg). It has shown mechanistic comparability to piperidine, allowing to extend the applicability of this method to Fmoc cleavage in general. In specific examples, DEAPA has shown superiority with regard to side reactions, resulting in products with higher purity. DEAPA is not in the list of controlled substances and even its price is lower than the price of piperidine.

The invention also provides degarelix, or pharmaceutically acceptable salt thereof, comprising not more than 1.0%, e.g., not more than 0.5%, not more than 0.1%, not more than 0.05%, not more than 0.04%, or not more than 0.03%, of hydantoin impurity relative to the degarelix or a pharmaceutically acceptable salt thereof. In some embodiments, the degarelix is substantially free of piperidine. In certain embodiments, the degarelix comprises 1 ppm to 1000 ppm DEAPA, 10 ppm to 500 ppm DEAPA, 50 ppm to 250 ppm DEAPA, 125 ppm to 750 ppm DEAPA, 125 ppm to 500 ppm DEAPA, or 200 ppm to 500 ppm DEAPA.

ABBREVIATIONS

Aph p-amino-phenylalanine
h hour
min minutes
GnRH Gonadotropin releasing hormone
SPPS Solid phase peptide synthesis
Fmoc-Aph(Hor)-OH 9-Fluorenylmethyloxycarbonyl-N(4)-(L-hydroorotyl)-4-aminophenylalanine
Fmoc-Phe-OH 9-Fluorenylmethyloxycarbonyl-L-phenylalanine
Aph(Hor) N(4)-(L-hydroorotyl)-4-aminophenylalanine
Hor Dihydroorotyl moiety
Hor-OH (L)dihydroorotic acid
Fmoc 9-Fluorenylmethyloxycarbonyl
Boc t-Butyloxycarbonyl
HPLC High performance liquid chromatography
DIPEA/DIEA Diisopropylethylamine
DEAPA 3-(Diethylamino)propylamine
TFA Trifluoroacetic acid
DMF N,N-dimethylformamide
DMA N,N-dimethylacetamide
NMP 1-methyl-2-pyrrolidone
NBP 1-butyl-2-pyrrolidone
ACN Acetonitrile
DCM Dichloromethane
DBF Dibenzofulvene
DIC Diisopropylcarbodiimide
TIS Tri-isopropylsilane
OxymaPure Ethyl 2-cyano-2-hydroxyimino-acetate
RRT Relative retention time
RT Room temperature
TM Target molecule
Trt-PS resin Polystyrenic trityl resin

EXAMPLES

The following examples provide detailed experimental conditions for the method of present invention and are intended to be illustrative and not limiting of all possible embodiments of the same.

Unless otherwise noted, all materials, solvents and reagents were obtained from commercial suppliers, of the best grade, and used without further purification.

Solid-phase synthesis of the peptides was carried out manually or using common peptide synthesizers, such as Biotage Syrowave instrument (automated syntheses) and Biotage MultiSynTech (semi automated syntheses).

HPLC-Methods

Examples 1-6: HPLC-MS analyses were performed on Agilent 1260 Infinity II system coupled to an electrospray ionization mass spectrometer (positive-ion mode, m/z=100-1500, fragmentor 30 V), using columns Agilent Zorbax-SB-C18 5 μm, 250×4.6 mm or Phenomenex Luna C18 5 μm, 250×4.6 mm; temperature: 25° C.; injection volume: 10 μL, UV: 220 nm, mobile phases: $H_2O$+0.08% TFA (A) and $CH_3CN$+0.08% TFA (B), flow: 0.5 mL/min or 1.0 mL/min.

Example 7: HPLC analyses were performed on Agilent 1260 Infinity II system, using columns Waters Cortecs C18 2.7 μm, 4.6×150 mm; temperature: 30° C.; injection volume: 10 μL, UV: 245 nm; pH 5.5 Phosphate Buffer: 25 mM Potassium Phosphate to pH 5.5; pH 3.5 Phosphate Buffer: 25 mM Potassium Phosphate to pH 3.5; mobile phases: 75% pH 5.5 Buffer: 25% $CH_3CN$ (A); 65% pH 3.5 Buffer: 35% $CH_3CN$ (B); flow: 1.0 mL/min, sample concentration 0.5 mg/ml; gradient: 0-5 min 0% B, 5-45 min f0-100% B, 45-46 min 100-0% B, 46-60 min 0% B.

Example 1

Monitoring of DBF-Amine Adduct Formation 50 mg of dry resin Fmoc-Gly-Trt-PS were swelled in 2 mL of DMF for 30 minutes. The resin was filtered and 0.75 mL 20% base solution (DEAPA, piperidine, TBA or TMG) in DMF-d6 was added on the resin and stirred for 30 min. The resin was filtered and the filtrate was straight analysed by $^1$H NMR spectroscopy in order to reveal the presence of DBF alone or the formation of the DBF-amine adduct (Scheme 1).

$^1$H NMR spectra demonstrated the formation of DBF-DEAPA adduct (FIG. 3) in DBF/DBF-DEAPA 1/1.8 ratio and the formation of DBF-piperidine adduct (FIG. 4) in ratio DBF/DBF-piperidine 1/7.7 ratio after 30 min.

No base-DBF adduct was observed with TBA or TMG.

Example 2

Full Fmoc-Based SPPS of H-Phe-L-Cys-Gly-OH and H-Phe-D-Cys-Gly-OH in DMF as Reference Compounds for Cys Racemization Tests The synthesis was carried out by using Fmoc-Gly-Trt-PS resin (200 mg, loading 1.1 mmol/g). After swelling of the resin in 2 mL of DMF, Fmoc protective group was removed by 20% piperidine in DMF (2×2 mL, 15 min each) and the resin was washed with DMF (4×2 mL). Fmoc-L-Cys(Trt)-OH (or Fmoc-D-Cys(Trt)-OH) and Fmoc-Phe-OH (three-fold excess with respect to the loading of the resin) were pre-activated by DIC and OxymaPure (three-fold excess of the reagents with respect to the loading of the resin) for 3 min and coupled to the resin in 60 min. After each coupling step the Fmoc protective group was removed by treating the peptide resin with a 20% piperidine in DMF (2×2 mL, 15 min each), and the resin was washed with DMF (4×2 mL). After Fmoc-cleavage of N-terminal alpha-amino group the peptide resin was washed with DMF (3×2 mL) and DCM (3×2 mL). Dry peptide resin was suspended in 5 mL of the mixture TFA/TIS/$H_2O$/1-dodecanethiol (92.5/2.5/2.5/2.5 v/v/v/v) and stirred for 2 h. The resin was filtered off and diisopropylether (20 mL) cooled to 4° C. was added to the solution. The peptide was filtered and dried in vacuo to obtain crude H-Phe-L-Cys-Gly-OH or H-Phe-D-Cys-Gly-OH as reference compounds for racemization tests.

HPLC-MS analysis gradient: 0-30 min 0-60% B; flow: 0.5 mL/min.

Example 3

Cys Racemization Tests During Full Fmoc-based SPPS Of H-PHE-L-Cys-Gly-OH in DMF with DEAPA and Piperidine as Deprotecting Agents Two SPPS of H-Phe-L-Cys-Gly-OH were conducted as reported above in Example 2, but using the following conditions for Fmoc group cleavage in parallel: 30% DEAPA or piperidine in DMF for 60 minutes.

HPLC-MS analysis gradient: 0-30 min 0-60% B; flow: 0.5 mL/min.

Racemization ratio (D/L %) in the preparation of H-Phe-Cys-Gly-OH was determined by HPLC % areas (A %) of the two diastereomers, and calculated as (H-Phe-D-Cys-Gly-OH A %)/(H-Phe-L-Cys-Gly-OH A %)×100. D/L % was <0.1 in both experiments.

Example 4

Full Fmoc-Based SPPS of H-D-Phe-Cys-Phe-D-Trp-Lys-Thr-Cys-Thr-ol (Linear Octreotide, II, SEQ ID NO: 1) with DEAPA or Piperidine as Fmoc-Cleaving Agent The synthesis was carried out by using Fmoc-Thr(tBu)-ol-Trt-PS resin (200 mg, loading 1.1 mmol/g). After swelling of the resin in 2 mL of DMF or NBP, Fmoc protective group was removed by 10% DEAPA in DMF (or 20% piperidine in DMF or NBP) (2×2 mL, 15 min each) and the resin was washed with DMF or NBP (4×2 mL). Fmoc-Cys(Trt)-OH, Fmoc-Thr(tBu)-OH, Fmoc-Lys(Boc)-OH, Fmoc-D-Trp(Boc)-OH, Fmoc-Phe-OH, Fmoc-Cys(Trt)-OH, Fmoc-D-Phe-OH (three-fold excess with respect to the loading of the resin) were pre-activated by DIC and OxymaPure (three-fold excess of the reagents with respect to the loading of the resin) for 3 min and coupled to the resin in 60 min. In case of the first inserted Fmoc-Cys(Trt)-OH ($Cys^7$ in the final sequence) the coupling was repeated a second time. After each coupling step the Fmoc protective group was removed by treating the peptide resin with 10% DEAPA in DMF (2×2 mL, 15 min each) or with 20% piperidine in DMF or NBP (2×2 mL, 15 min each), and the resin was washed with DMF or NBP (4×2 mL). After Fmoc cleavage of the N-terminal amino group the peptide resin was washed with DMF or NBP (3×2 mL) and DCM (3×2 mL). Dry peptide resin was suspended in 5 mL of the mixture TFA/TIS/1-dodecanethiol (90/5/5 v/v/v) and stirred for 4 h. The resin was filtered off and diisopropylether (20 mL) cooled to 4° C. was added to the solution. The peptide was filtered and dried in vacuo to obtain crude linear octreotide (II). HPLC purities calculated as sum of all target molecule adducts are reported in Table 2. It is worth noticing that all the species reported in Table 2 are not impurities but precursors of the final Octreotide (TM=target molecule).

HPLC-MS analysis gradient: 0-15 min 20-40% B; flow: 0.5 mL/min.

TABLE 2

HPLC Purity of Linear Octreotide (II) in DMF with 10% DEAPA in DMF or with 20% piperidine in DMF or NBP as deprotecting agent

| | | Fmoc cleavage conditions | | |
| --- | --- | --- | --- | --- |
| Compound | RRT | DMF 10% DEAPA | DMF 20% Piperidine | NBP 20% Piperidine |
| Cyclized N,O shift | 0.83 | — | 1.4 | — |
| Unknown | 0.84 | 0.7 | — | — |
| Cyclized | 0.88 | 0.7 | 3.8 | 2.4 |
| TM-N,O shift 1 | 0.92 | — | — | 0.7 |
| TM-N,O shift 2 | 0.95 | 3.5 | 5.1 | 4.2 |
| TM + $CO_2$ | 0.97 | — | 9.5 | 4.7 |
| TM | 1.00 | 83.2 | 68.3 | 76.8 |
| Unknown | 1.09 | — | 1.2 | 0.5 |
| TM + tBu | 1.14 | 9.0 | 9.5 | 7.2 |
| TM + tBu2 | 1.26 | 2.9 | 1.2 | 3.0 |
| Product purity (%)[a] | | 99.3 | 98.8 | 99.0 |
| Sum of unknown (%) | | 0.7 | 1.2 | 1.0 |

[a]HPLC purity calculated as sum of all target product adducts

Example 5

Full Fmoc-Based SPPS of H-Ala-Lys-Asp-Gly-Tyr-Ile-OH (III, SEQ ID NO: 2) with Piperidine/DMF Fmoc Cleavage for Aspartimide Formation Detection The synthesis was carried out by using Fmoc-Ile-Trt-PS resin (800 mg, loading 1.1 mmol/g). After swelling of the resin in 2 mL of DMF, Fmoc protective group was removed by 20% piperidine in DMF (2×2 mL, 15 min each) and the resin was washed with DMF (4×2 mL). Fmoc-Tyr(tBu)-OH, Fmoc-Gly-OH, Fmoc-Asp(OtBu)-OH, Fmoc-Lys(Boc)-OH, Fmoc-Ala-OH (three-fold excess with respect to the loading of the resin) were pre-activated by DIC and OxymaPure (three-fold excess of the reagents with respect to the loading of the resin) for 3 min and coupled to the resin for 60 min. After each coupling step the Fmoc protective group was removed by treating the peptide resin with 20% piperidine in DMF (2×2 mL, 15 min each), and the resin was washed with DMF (4×2 mL). After Fmoc cleavage of N-terminal amino group the peptide resin was washed with DMF (3×2 mL) and DCM (3×2 mL). 100 mg dry peptide resin were suspended in 3 mL of the mixture TFA/TIS/$H_2O$ (90/5/5 v/v/v) and stirred for 2 h. The resin was filtered off and diisopropylether (10 mL) cooled to 4° C. was added to the solution. The peptide was filtered and dried in vacuo to obtain crude H-Ala-Lys-Asp-Gly-Tyr-Ile-OH (II) with an HPLC purity of 97.4% and Aspartimide impurity (IV) of 2.6%.

HPLC-MS analysis gradient: 0-30 min 10-40% B; flow: 0.5 mL/min.

Example 6

Stress Stability Test of H-Ala-Lys-Asp-Gly-Tyr-Ile-OH (II, SEQ ID NO: 2) with Piperidine, DEAPA, TMG and TBA in DMF or NBP 100 mg of dry resin H-Ala-Lys-Asp-Gly-Tyr-Ile-Trt-PS (prepared as described in Example 2) were swelled in 2 mL of DMF or NBP for 30 minutes. The resin was filtered and a 2 mL solution of 10% DEAPA (or 20% piperidine, 5% TMG, 20% TBA) in DMF or NBP was added to the resin and stirred for 4 hours at RT. The resin was filtered, washed with DMF or NBP (3×2 mL) and with DCM (3×2 mL). Dry peptide resin was suspended in 3 mL of the mixture TFA/TIS/$H_2O$ (90/5/5 v/v/v) and stirred for 2 h. The resin was filtered off and diisopropylether (10 mL) cooled to 4° C. was added to the solution. The peptide was filtered and dried in vacuo to obtain crude H-Ala-Lys-Asp-Gly-Tyr-Ile-OH (II) and aspartimide impurity (III) in different ratios according to the used conditions.

Table 1 in the description lists the results. ΔAsp indicates the difference between the aspartimide amount formed after stress tests (including piperidides if present) and that arising from the hexapeptide synthesis (2.6%, see Example 2).

HPLC-MS analysis gradient: 0-30 min 10-40% B; flow: 0.5 mL/min.

Example 7

Stability of Degarelix in the Presence of DEAPA

A sample of degarelix, as a lyophilized powder of about 99% purity, was dissolved in DMF with 10% DEAPA at two different concentrations: about 170 g/L (Test 1) and about 17 g/L (Test 2). The stability at RT was followed for 24 h at four check points, i.e. t0, 1 h (t1), 4 h (t2) and 24 h (t3).

Superimposed HPLC profiles are shown in FIG. 3 (Test 1) and FIG. 4 (Test 2).

Test 1: Profile not changed after 24 h. Only specified impurity RRT 0.85 (X, unknown), not present at t0, increased to a value of 0.06% at t3 (purity change from 99.17 to 99.10%).

Hydantoin impurity (VI) at RRT 1.03 did not increase: 0.10% at both t0 and t3.

Test 2: Profile not changed after 24 h. Only specified impurity RRT 0.85 (X, unknown), not present at t0, increased to a value of 0.04% at t3 (purity change from 99.18% to 99.10%).

Hydantoin impurity (VI) at RRT 1.03 did not increase: 0.09% at both t0 and t3.

Example 8

Stability of Degarelix in the Presence of 10% Base

A sample of Degarelix, as a lyophilized powder of about 99% of purity, was dissolved at a concentration of 17 g/L in DMF with 10% of piperidine, TMG, TBA or DEAPA. The stability at RT was measured by HPLC at t=0 (t0), t=8 hr (t1), and t=24 hr (t3) using an Agilent 1260 Infinity II system, using a column Waters Xterra Shield RP18, 3.5 μm, 4.6×150 mm; temperature: 25° C.; sample concentration 0.5 mg/mL; injection volume: 10 μL; flow: 0.7 mL/min; buffer: 65% 40 mM ammonium acetate, pH 10:35% ACN; elution: isocratic, 0-30 min 100% buffer; detection: UV 245 nm.

The amounts of degarelix and hydantoin impurity after 24 hours at room temperature are summarized in Table 3.

TABLE 3

| Duration | Base solution | Degarelix % | Hydantoin VI % |
|---|---|---|---|
| 0 | None | 99.97 | 0.03 |
| 24 hr | Piperidine | 99.96 | 0.04 |
| 24 hr | TMG | 98.7 | 1.3 |
| 24 hr | TBA | 99.96 | 0.04 |
| 24 hr | DEAPA | 99.97 | 0.03 |

Superimposed HPLC profiles of degarelix treated with DEAPA are shown in FIG. 5. The results of this example demonstrate that the amount of hydantoin impurity (VI) was unchanged after 24-hours treatment with DEAPA.

What is claimed is:

1. A method for cleaving Fmoc from one or more Fmoc protected amino groups, wherein the method comprises a step of contacting the one or more Fmoc protected amino groups with a solution comprising 3-(diethylamino)propylamine (DEAPA).

2. The method according to claim 1, wherein the concentration of DEAPA in the solution ranges from 5 to 30 vol % or from 10 to 20 vol %.

3. The method according to claim 2, wherein the concentration of DEAPA in the solution is 10 vol %.

4. The method according to claim 1, wherein the solution further comprises a solvent selected from the group consisting of N,N-dimethylformamide, N-methylpyrrolidone, N-butylpyrrolidone and mixtures thereof.

5. The method according to claim 4, wherein the solution comprises 10 vol % DEAPA in N,N-dimethylformamide.

6. The method according to claim 1, wherein the cleaving of the Fmoc is performed on a peptide in solid phase peptide synthesis.

7. The method according to claim 6, wherein the peptide comprises at least one aspartic acid.

8. The method according to claim 6, wherein the peptide is selected from the group consisting of degarelix, octreotide, exenatide, etelcalcetide and glucagon.

9. The method according to claim 8, wherein the peptide is degarelix and the degarelix is prepared by using a protected amino acid selected from the group consisting of Fmoc-Aph(Hor)-OH, Fmoc-Aph(PG)-OH, Fmoc-Phe(NO$_2$)—OH and Fmoc-D-Phe(NO$_2$)—OH, wherein PG is an amino protective group selected from tert-butyloxycarbonyl, formyl, allyloxycarbonyl and benzyloxycarbonyl.

10. A method for the preparation of a peptide by Fmoc-based solid phase peptide synthesis, wherein the method comprises a step of contacting the one or more Fmoc protected amino groups with a solution comprising 3-(diethylamino)propylamine (DEAPA), thereby cleaving the Fmoc from the one or more Fmoc protected amino groups.

11. The method according to claim 10, wherein the concentration of DEAPA in the solution is in the range from 5 to 30 vol % or from 10 to 20 vol %, or is 10 vol %.

12. The method according to claim 10, wherein the solution further comprises a solvent selected from the group consisting of N,N-dimethylformamide, N-methylpyrrolidone, N-butylpyrrolidone and mixtures thereof.

13. The method according to claim 10, wherein the peptide comprises at least one aspartic acid.

14. The method according to claim 10, wherein the peptide is selected from the group consisting of degarelix, octreotide, exenatide, etelcalcetide and glucagon.

* * * * *